United States Patent
Kashiwagi et al.

(10) Patent No.: US 7,639,779 B2
(45) Date of Patent: Dec. 29, 2009

(54) APPARATUS FOR AND METHOD OF CAPTURING RADIATION IMAGE

(75) Inventors: Nobuhiko Kashiwagi, Odawara (JP); Hajime Nakata, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 16 days.

(21) Appl. No.: 12/133,774

(22) Filed: Jun. 5, 2008

(65) Prior Publication Data

US 2009/0022273 A1 Jan. 22, 2009

(30) Foreign Application Priority Data

Jul. 20, 2007 (JP) .............................. 2007-188928

(51) Int. Cl.
*A61B 6/04* (2006.01)
(52) U.S. Cl. ............................. 378/37; 378/96; 378/97; 378/165
(58) Field of Classification Search ................... 378/37, 378/62, 91, 96, 97, 98.7, 108–112, 117, 162, 378/163, 165
See application file for complete search history.

(56) References Cited

U.S. PATENT DOCUMENTS 5,485,501 A 1/1996 Aichinger
6,751,285 B2 * 6/2004 Eberhard et al. ............... 378/37
7,431,500 B2 * 10/2008 Deych et al. ................. 378/207

FOREIGN PATENT DOCUMENTS

| JP | 07-153592 A | 6/1995 |
| JP | 2003-115399 A | 4/2003 |
| JP | 2004-154409 A | 6/2004 |

\* cited by examiner

*Primary Examiner*—Jurie Yun
(74) *Attorney, Agent, or Firm*—Sughrue Mion, PLLC (57) ABSTRACT

An irradiation dose calculator calculates a pre-exposure-mode-required irradiation dose using the thickness of a breast which measured by a thickness measuring unit, as a parameter, and the irradiation time of a pre-exposure mode is controlled to apply a radiation to the breast in the pre-exposure mode. According to the dose of the radiation detected by a dose detecting sensor in the pre-exposure mode, the irradiation dose calculator calculates a main-exposure-mode-required irradiation dose, and the irradiation time of a main exposure mode is controlled to apply the radiation to the breast in the main exposure mode, thereby capturing a radiation image of the breast.

15 Claims, 11 Drawing Sheets

APPARATUS FOR AND METHOD OF CAPTURING RADIATION IMAGE

BACKGROUND OF THE INVENTION

1. Field of the Invention

The present invention relates to an apparatus for and a method of capturing a radiation image by applying a radiation emitted from a radiation source to a breast and detecting the radiation that has passed through the breast with a radiation detector.

2. Description of the Related Art

In the medical field, for example, it has been customary to apply a radiation to a subject and detect the radiation that has passed through the subject with a radiation detector, thereby capturing a radiation image of the subject.

One known radiation detector comprises a solid-state detector including a matrix of charge collecting electrodes formed on an insulating substrate and a radiation conductor disposed on the charge collecting electrodes for generating electric charges depending on the radiation that is applied to the radiation detector. The electric charges generated by the radiation conductor and representing a radiation image are collected by the charge collecting electrodes and temporarily stored in an electric storage unit. The collected electric charges are converted into an electric signal, which is output from the radiation detector. Other known radiation detectors include a radiation detector comprising a charge-coupled device (CCD) and a radiation detector comprising a combination of amorphous silicon and a scintillator. Furthermore, a stimulable phosphor panel which, when exposed to an applied radiation (X-rays, $\alpha$-rays, $\beta$-rays, $\gamma$-rays, electron beams, ultraviolet radiation, or the like), stores part of the energy of the radiation, and, when subsequently exposed to applied stimulating light such as laser beam, visible light, or the like, emits photo-stimulated luminescence in proportion to the stored energy of the radiation, may also be used as a radiation detector.

In order to obtain a high-quality radiation image captured by a radiation detector, it is necessary to set an appropriate irradiation dose depending on the radiation transmittance of the region to be imaged, of the subject. If the region to be imaged is a breast, then since the radiation transmittance greatly differs depending on the thickness of the breast and the density of the mammary gland, it is highly important to adjust the required irradiation dose depending on the state of the breast and control the radiation to prevent the breast from being irradiated with an excessive amount of radiation.

Japanese Laid-Open Patent Publication No. 7-153592 and Japanese Laid-Open Patent Publication No. 2003-115399 disclose a process of performing a pre-exposure mode to apply a low dose of radiation to a subject, detect the dose of the radiation that has passed through the subject with a radiation detector, and calculate a irradiation dose required to capture a radiation image of the subject and thereafter performing a main exposure mode to apply a radiation based on the calculated irradiation dose to the subject to capture a radiation image of the subject.

However, inasmuch as the radiation that reaches the radiation detector greatly differs depending on the thickness of the breast and the density of the mammary gland, if the irradiation dose in the pre-exposure mode is set to a constant level as disclosed in Japanese Laid-Open Patent Publication No. 7-153592 and Japanese Laid-Open Patent Publication No. 2003-115399, a radiation having a dose which needs to be detected may not be applied to the radiation detector or an excessive radiation may be applied to the radiation detector, so that the radiation detector may fail to detect the irradiation dose highly accurately. If an excessive radiation greater than the irradiation dose required to capture a radiation image is applied to the breast in the pre-exposure mode, then an unnecessary radiation is applied to the breast, tending to make the main exposure mode impossible to perform.

SUMMARY OF THE INVENTION

It is a general object of the present invention to provide an apparatus for and a method of capturing a radiation image by highly accurately calculating an irradiation dose required to capture a radiation image of a breast and by preventing the breast from being irradiated with an excessive radiation.

An object of the present invention is to provide an apparatus for and a method of capturing a radiation image of high quality based on a highly accurately calculated irradiation dose of a radiation.

Another object of the present invention is to provide an apparatus for and a method of capturing a radiation image without causing a moving grid to develop irregularities in the radiation image.

The above and other objects, features, and advantages of the present invention will become more apparent from the following description when taken in conjunction with the accompanying drawings in which preferred embodiments of the present invention is shown by way of illustrative example.

DESCRIPTION OF THE PREFERRED EMBODIMENTS

Figure 1:
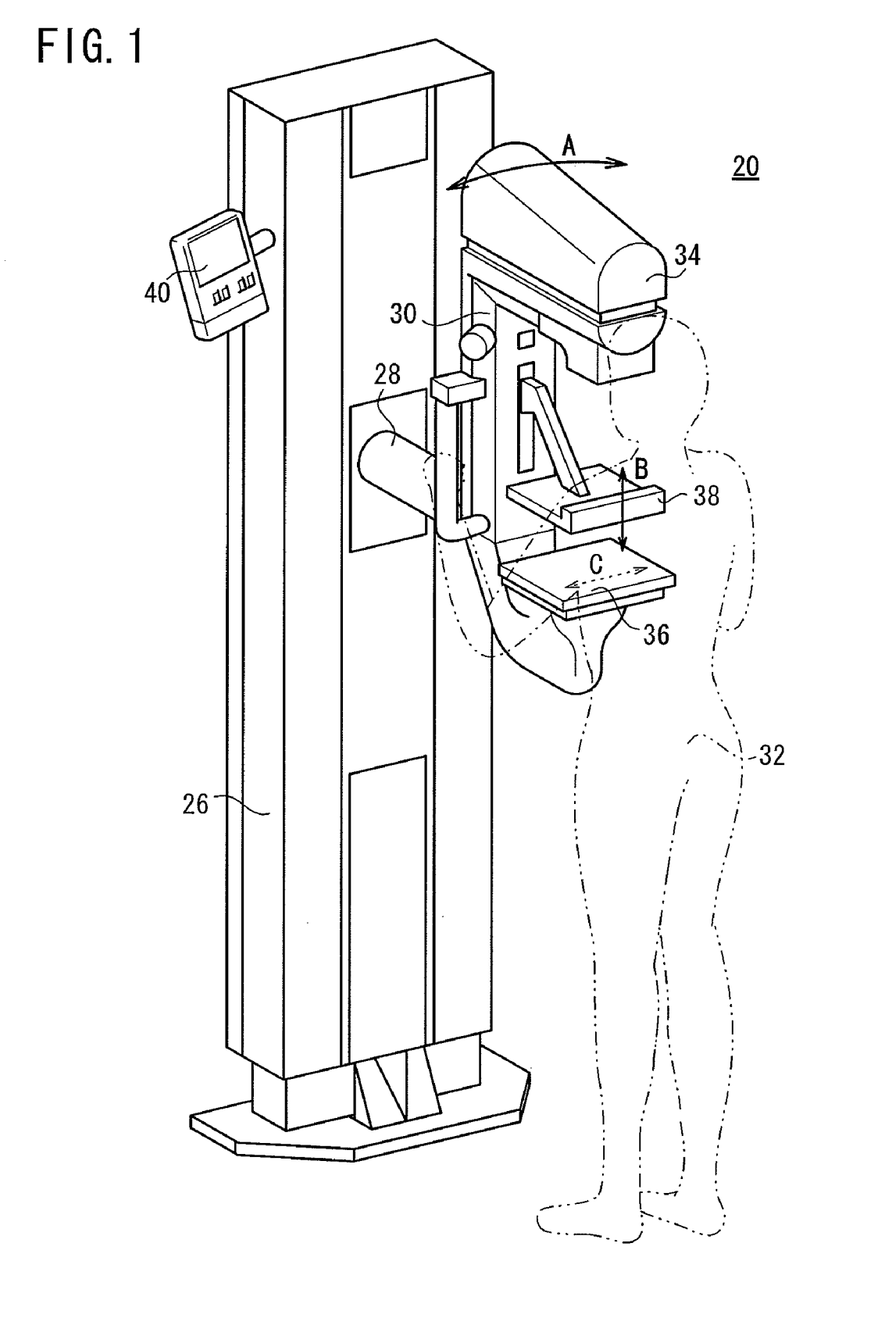
FIG. 1 is a perspective view of a mammographic system according to an embodiment of the present invention.

FIG. 1 shows in perspective a mammographic system 20 to which an apparatus for and a method of capturing a radiation image according to an embodiment of the present invention are applied.

As shown in FIG. 1, the mammographic system 20 includes an upstanding base 26, a vertical arm 30 fixed to a horizontal swing shaft 28 disposed substantially centrally on the base 26, a radiation source housing unit 34 storing a radiation source 22 (see FIG. 3) for applying a radiation to a breast 44 (see FIG. 2) to be imaged of a subject 32 and fixed to an upper end of the arm 30, an image capturing base 36 housing a solid-state detector 24 (see FIGS. 2 and 3) for obtaining a radiation image by detecting a radiation X that has passed through the breast 44 and fixed to a lower end of the arm 30, and a presser plate 38 for pressing and holding the breast 44 against the image capturing base 36.

When the arm 30, to which the radiation source housing unit 34 and the image capturing base 36 are secured, is angularly moved about the swing shaft 28 in the directions indicated by the arrow A, an image capturing direction with respect to the breast 44 of the subject 32 is adjusted. The presser plate 38 is connected to the arm 30 and disposed between the radiation source housing unit 34 and the image capturing base 36. The presser plate 38 is vertically displaceable along the arm 30 in the directions indicated by the arrow B.

To the base 26, there is connected a display control panel 40 for displaying image capturing information including an image capturing region, an image capturing direction, etc. of the subject 32 detected by the mammographic system 20, the ID information of the subject 32, etc., and setting these information, if necessary.

Figure 2:
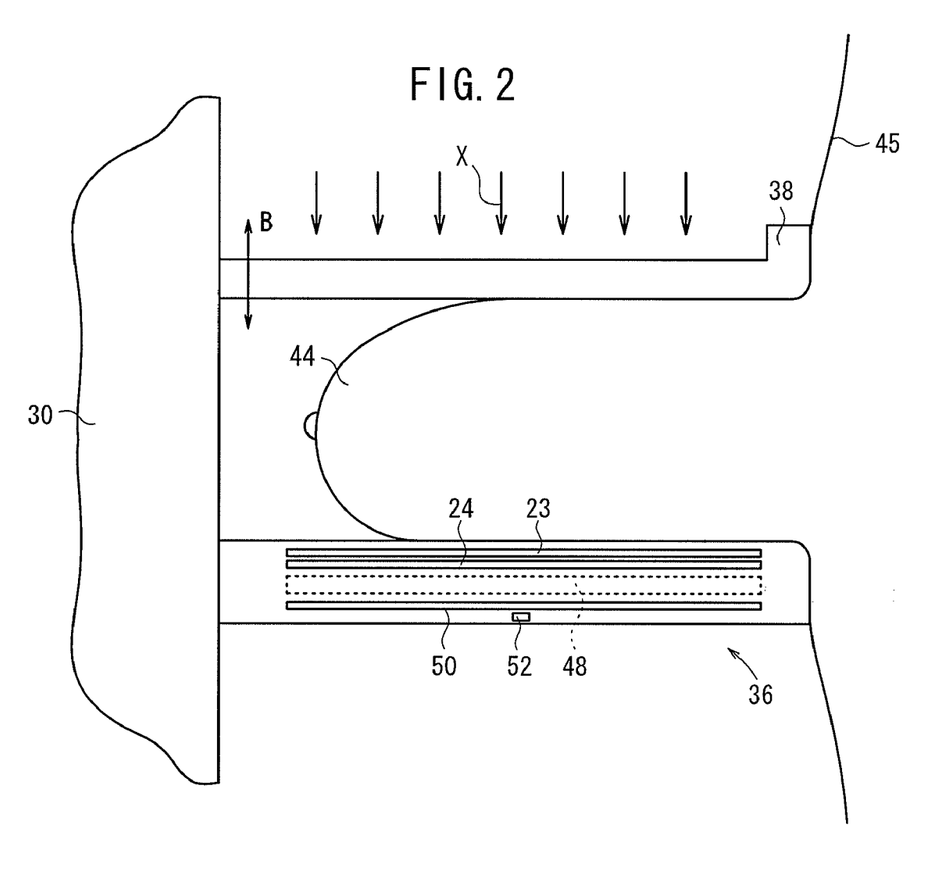
FIG. 2 is a fragmentary vertical elevational view, partly in cross section, showing internal structural details of an image capturing base of the mammographic system according to the embodiment of the present invention.
Figure 3:
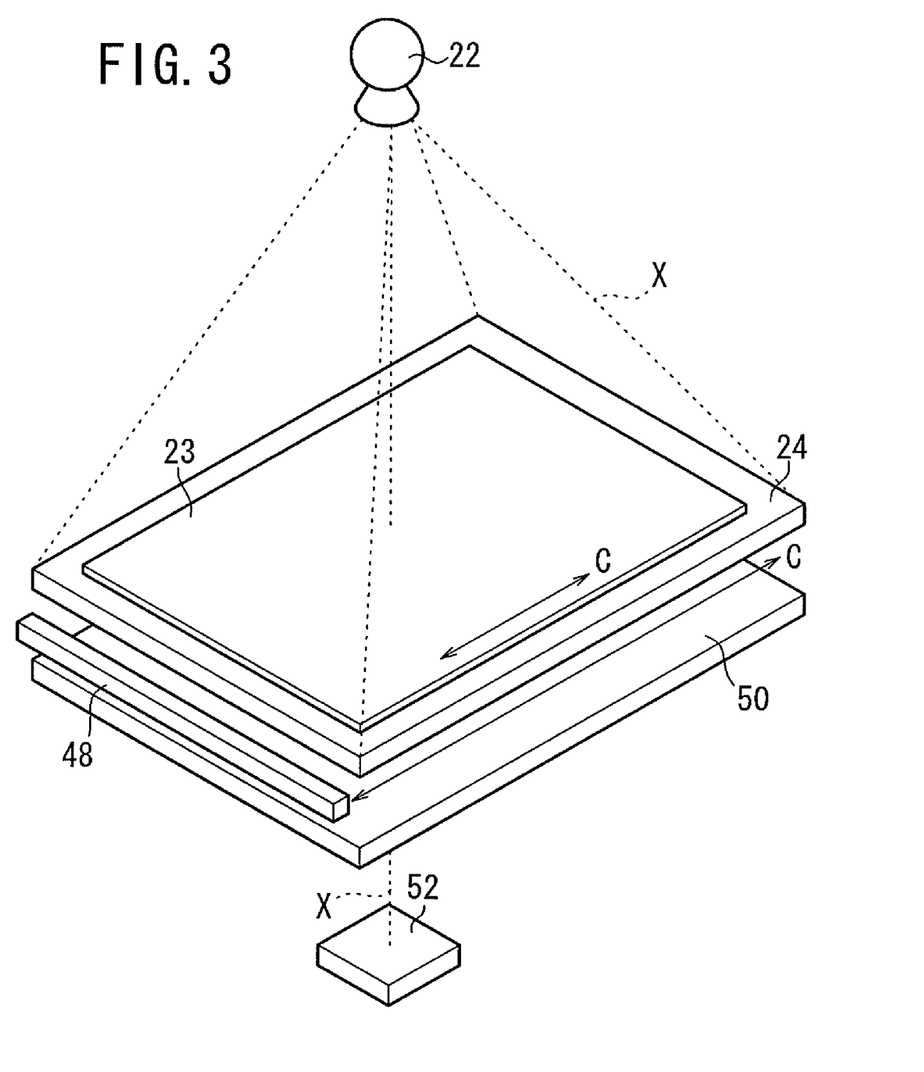
FIG. 3 is a perspective view showing internal structural details of the image capturing base of the mammographic system according to the embodiment of the present invention.

FIGS. 2 and 3 show internal structural details of the image capturing base 36 of the mammographic system 20. In FIG. 2, the breast 44 of the subject 32 is shown as being placed between the image capturing base 36 and the presser plate 38. The reference numeral 45 represents a chest wall.

The image capturing base 36 houses therein a moving grid 23 for removing scattered rays of the radiation X emitted from the radiation source 22, a solid-state detector 24 for storing a radiation image based on the radiation X that has passed through the breast 44 as an electric charge information, a reading light source 48 for applying reading light to the solid-state detector 24 to read the electric charge information stored in the solid-state detector 24, an erasing light source 50 for applying erasing light to the solid-state detector 24 to remove unwanted electric charges stored in the solid state detector 24, and a dose detecting sensor 52 for detecting the dose of the radiation X that has passed through the solid-state detector 24.

The moving grid 23 is made of a substance for absorbing the radiation X and a substance for passing the radiation X through, the substances being alternately arranged in a striped or grid-like pattern. The moving grid 23 is movable or vibratable at a predetermined speed in the directions indicated by the arrow C.

The solid-state detector 24 comprises a direct-conversion, light-reading radiation solid-state detector, for example. The solid-state detector 24 stores radiation image of the radiation X that has passed through the breast 44 as an electrostatic latent image, and generates an electric current depending on the electrostatic latent image when the solid-state detector 24 is scanned by the reading light applied from the reading light source 48.

The solid-state detector 24 may be a detector as disclosed in Japanese Laid-Open Patent Publication No. 2004-154409, for example. More specifically, the solid-state detector 24 comprises a laminated assembly of a first electrically conductive layer disposed on a glass substrate for passing the radiation X therethrough, a recording photoconductive layer for generating electric charges upon exposure to the radiation X, a charge transport layer which acts substantially as an electric insulator with respect to latent image polarity electric charges developed in the first electrically conductive layer and which acts substantially as an electric conductor with respect to transport polarity charges which are of a polarity opposite to the latent image polarity electric charges, a reading photoconductive layer for generating electric charges and making itself electrically conductive upon exposure to the reading light, and a second electrically conductive layer which is permeable to the radiation X. An electric energy storage region is provided in the interface between the recording photoconductive layer and the charge transport layer.

Each of the first electrically conductive layer and the second electrically conductive layer provides an electrode. The electrode provided by the first electrically conductive layer comprises a two-dimensional flat electrode. The electrode provided by the second electrically conductive layer comprises a plurality of linear electrodes spaced at a predetermined pixel pitch for detecting the electric charge information of the radiation image to be recorded, as an image signal. The linear electrodes are arranged in an array along a main scanning direction, and extend in an auxiliary scanning direction.

The reading light source 48 includes, for example, a line light source comprising a linear array of LED chips and an optical system for applying a line of reading light emitted from the line light source to the solid-state detector 24. The linear array of LED chips extends perpendicularly to the direction in which the linear electrodes of the second electrically conductive layer of the solid-state detector 24 extend. The line light source moves along the directions, i.e., the directions indicated by the arrow C, in which the linear electrodes extend to expose and scan the entire surface of the solid-state detector 24.

The erasing light source 50 comprises a plurality of LED chips which can emit and quench light in a short period of time and which have very short persistence. The LED chips are arrayed along a two-dimensional plane parallel to the solid-state detector 24.

The dose detecting sensor 52 comprises a sensor for detecting the dose of the radiation X which has passed through the breast 44 near the mammary gland thereof. If necessary, the dose detecting sensor 52 may comprise a plurality of sensors.

Figure 4:
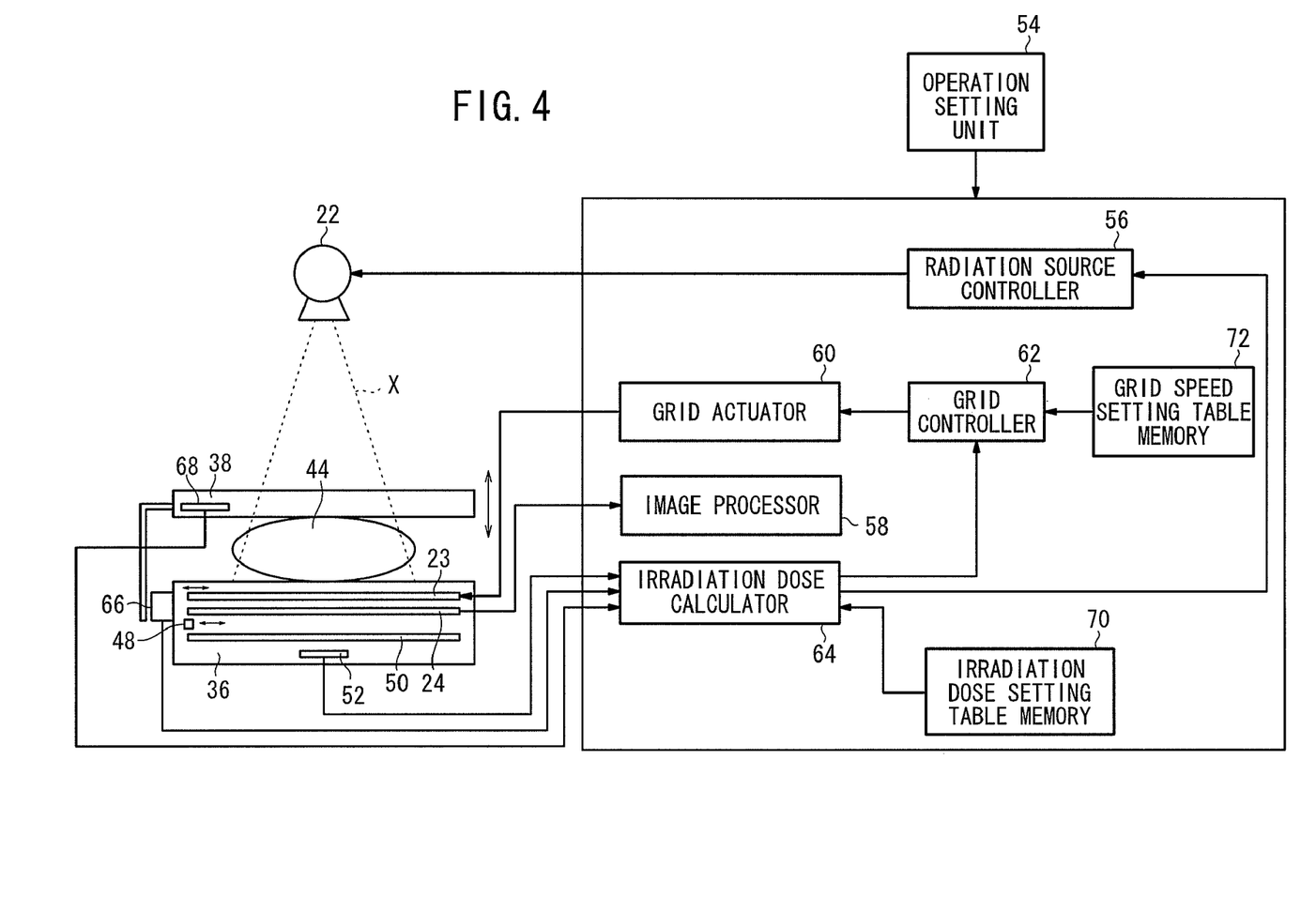
FIG. 4 is a block diagram of a control circuit of the mammographic system according to the embodiment of the present invention.

FIG. 4 shows in block form a control circuit of the mammographic system 20.

As shown in FIG. 4, the mammographic system 20 includes an operation setting unit 54 (radiation quality information setting unit) for setting subject information with respect to the age, sex, body type, subject identification number, etc. of the subject 32, image capturing conditions and an image capturing process for capturing a radiation image, etc., a radiation source controller 56 for controlling the radiation source 22 according to the set image capturing conditions including a tube current, a tube voltage, the types of a target and a filter in the radiation source 22, a calculated irradiation dose of the radiation X, a calculated irradiation time, an image processor 58 for processing the radiation image of the breast 44 which is acquired from the solid-state detector 24, a grid controller 62 for controlling the speed at which the moving grid 23 moves through a grid actuator 60, according to the calculated irradiation dose of the radiation X, and an irradiation dose calculator 64 (a pre-exposure-mode-required irradiation dose calculator, a main-exposure-mode-required irradiation dose calculator) for calculating an irradiation dose of the radiation X that is required to capture a radiation image.

The irradiation dose calculator 64 is supplied with data of the dose of the radiation X which is detected by the dose detecting sensor 52, data of the thickness of the breast 44 measured by a thickness measuring unit 66 along the direction in which the radiation passes when the breast 44 is pressed by the presser plate 38, data of the pressure applied to the breast 44 measured by a pressure measuring unit 68 when the breast 44 is pressed by the presser plate 38, data of the image capturing conditions set by the operation setting unit 54, and data of an irradiation dose setting table stored in an irradiation dose setting table memory 70. The irradiation dose calculator 64 selects irradiation doses required in a pre-exposure mode and a main exposure mode which correspond to a combination of a dose, a breast thickness, an applied pressure, image capturing conditions, etc., using the irradiation dose setting table, or calculates irradiation doses required in a pre-exposure mode and a main exposure mode by interpolating data stored in the irradiation dose setting table, and supplies the selected or calculated irradiation doses to the radiation source controller 56 and the grid controller 62. The pre-exposure mode refers to a process of applying a small dose of radiation X to the breast 44 in order to calculate the irradiation dose of the radiation X which is required to acquire a desired radiation image. The main exposure mode refers to a process of applying the radiation X according to the irradiation dose calculated in the pre-exposure mode to the breast 44 for capturing a radiation image thereof.

The grid controller 62 is supplied with the data of the irradiation doses calculated by the irradiation dose calculator 64 and data of a grid speed setting table stored in a grid speed setting table memory 72. The grid controller 62 selects moving speeds of the moving grid in the pre-exposure mode and the main exposure mode which correspond to the irradiation times of the radiation X that are required to obtain necessary irradiation doses, or calculates moving speeds of the moving grid in the pre-exposure mode and the main exposure mode by interpolating data of the grid speed setting table, and supplies the selected or calculated moving speeds to the grid actuator 60.

The mammographic system 20 according to the present embodiment is basically constructed as described above. Operation of the mammographic system 20 will be described below with reference to a flowchart shown in FIG. 5.

Figure 5:
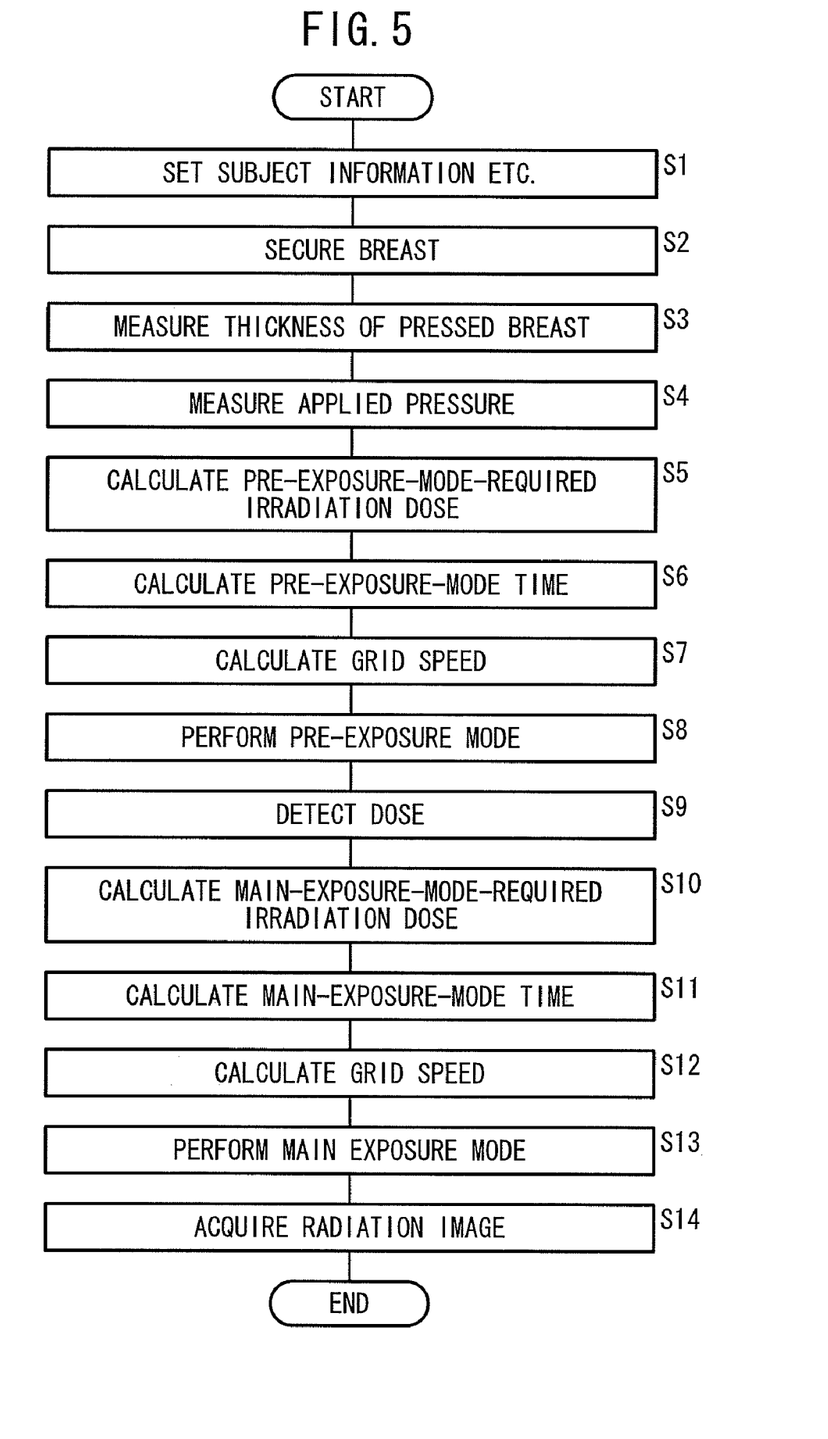
FIG. 5 is a flowchart of an operation sequence of the mammographic system according to the embodiment of the present invention.

Using the operation setting unit 54 of the mammographic system 20, the operator, who is typically a radiological technician, sets subject information, image capturing conditions, an image capturing process, etc. (step S1). The subject information includes information as to the age, sex, body type, subject identification number, etc. of the subject 32, and can be acquired from an ID card or the like owned by the subject 32. The image capturing conditions include a tube current, a tube voltage, the types of a target and a filter, an irradiation dose of the radiation X, etc. for acquiring a suitable radiation image depending on the breast 44 which is a region to be imaged of the subject 32. The image capturing process represents information including a region to be imaged that is specified by the doctor, an image capturing direction that is specified by the doctor, etc. These information can be displayed on the display control panel 40 of the mammographic system 20 for confirmation. If the mammographic system 20 is connected to a network, these information can be acquired from a higher-level apparatus through the network.

Then, the operator places the mammographic system 20 into a certain state according to the specified image capturing process. For example, the breast 44 may be imaged as a cranio-caudal view (CC) taken from above, a medio-lateral view (ML) taken from a lateral view, or a medio-lateral oblique view (MLO) taken from an oblique view. Depending on the information of a selected one of these image capturing directions, the operator turns the arm 30 about the swing shaft 28. In FIG. 1, the mammographic system 20 is set to take a cranio-caudal view (CC) of the breast 44.

Then, the operator positions the breast 44 of the subject 32 with respect to the mammographic system 20. For example, the operator places the breast 44 on the image capturing base 36, and thereafter lowers the presser plate 38 toward the image capturing base 36 to hold the breast 44 between the image capturing base 36 and the presser plate 38, as shown in FIG. 2 (step S2).

After the breast 44 has been placed securely between the image capturing base 36 and the presser plate 38, the thickness measuring unit 66 measures the thickness of the pressed breast 44 along the direction in which the radiation X passes, and supplies the measured data to the irradiation dose calculator 64 (step S3). The pressure measuring unit 68 measures the pressure applied by the presser plate 38 to the breast 44, and supplies the measured data to the irradiation dose calculator 64 (step S4).

The irradiation dose calculator 64 reads a corresponding irradiation dose from the irradiation dose setting table memory 70 based on the measured data of the breast thickness and the applied pressure and the image capturing conditions set in the operation setting unit 54, and calculates an irradiation dose required in a pre-exposure mode (step S5).

For example, if the breast thickness is small, then since the transmittance of the radiation X is high, the dose detecting sensor 52 can highly accurately detect the dose of the radiation X that has passed through the breast 44, with a low irradiation dose. If the applied pressure is low, then since the density of the mammary gland of the breast 44 is considered to be small and the transmittance of the radiation X is considered to be high, the dose detecting sensor 52 can also highly accurately detect the dose of the radiation X that has passed through the breast 44 with a low irradiation dose. The dose of the radiation X that reaches the dose detecting sensor 52 depends upon the tube voltage set in the radiation source 22 and the radiation quality information comprising image capturing conditions such as the types of a target and a filter, etc.

The irradiation dose setting table stored in the irradiation dose setting table memory 70 represents pre-exposure-mode-required irradiation doses for the dose detecting sensor 52 to detect the dose of the radiation X highly accurately, based on combinations of breast thicknesses, applied pressures, and radiation quality information. The irradiation dose calculator 64 reads a pre-exposure-mode-required irradiation dose corresponding to the entered data from the irradiation dose setting table stored in the irradiation dose setting table memory 70. If no corresponding pre-exposure-mode-required irradiation dose is stored in the irradiation dose setting table memory 70, then the irradiation dose calculator 64 may calculate a desired pre-exposure-mode-required irradiation dose by interpolating the existing pre-exposure-mode-required irradiation doses. Instead of using the irradiation dose setting table memory 70, the irradiation dose calculator 64 may have set therein a calculating formula including parameters representative of a breast thickness, an applied pressure, and radiation quality information, and may calculate a pre-exposure-mode-required irradiation dose according to the calculating formula.

The pre-exposure-mode-required irradiation dose read or calculated by the irradiation dose calculator 64 is supplied to the radiation source controller 56 and the grid controller 62. The irradiation dose calculator 64 calculates a pre-exposure-mode time for obtaining the pre-exposure-mode-required irradiation dose (step S6). The irradiation dose of the radiation X is determined by the product (mAs value) of the tube current (mA) of the radiation source 22 and the irradiation time (sec) of the radiation X. Therefore, if the tube current is constant, then the pre-exposure-mode time can easily be calculated from the pre-exposure-mode-required irradiation dose.

Figure 6:
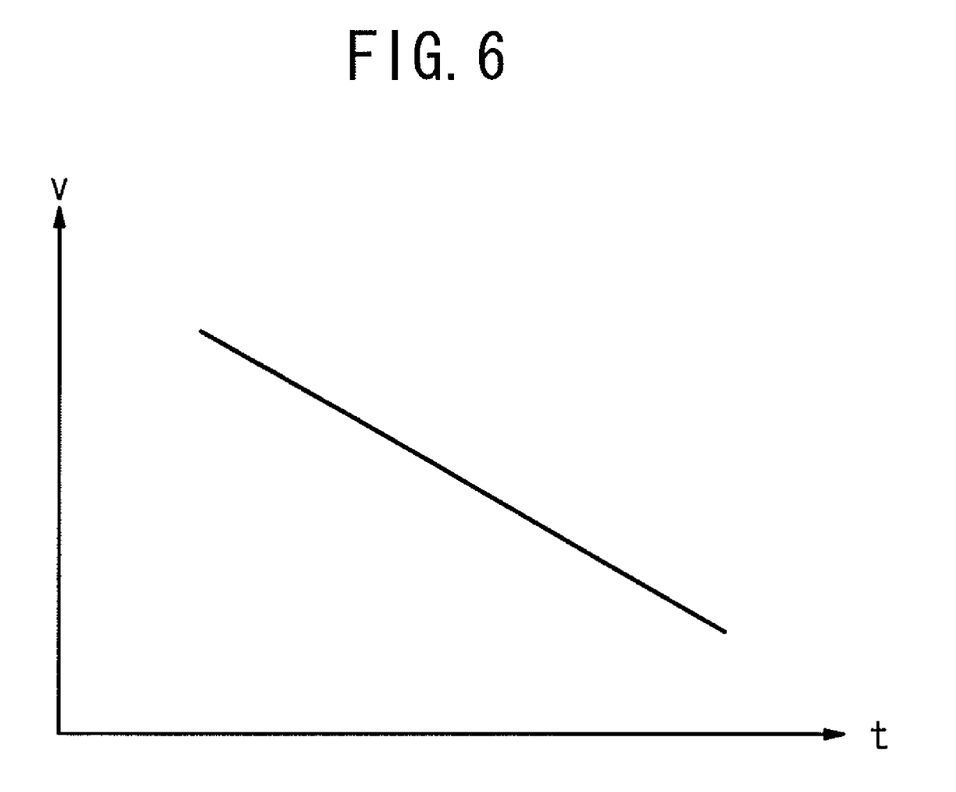
FIG. 6 is a graph showing the relationship between the irradiation time of a radiation and the grid speed.

According to the calculated pre-exposure-mode time, the grid controller 62 calculates a moving speed of the moving grid 23 (step S7). If the irradiation time of the radiation X is short, then since the distance that the moving grid moves during the irradiation time is small, a shadow of the moving grid 23 is formed in the radiation image captured by the solid-state detector 24. To avoid this drawback, the relationship between the irradiation time t and the moving speed v of the moving grid 23 for not forming a shadow of the moving grid 23, as shown in FIG. 6, is stored as a grid speed setting table in the grid speed setting table memory 72. The grid controller 62 determines a moving speed of the moving grid 23 from the grid speed setting table.

Thereafter, the radiation source controller 56 controls the radiation source 22 according to the calculated pre-exposure-mode time to apply the radiation X to the breast 44 in the pre-exposure mode (step S8). At this time, the grid controller 62 controls the grid actuator 60 to move the moving grid 23 at the moving speed calculated in step S7 in the direction indicated by the arrow C (FIG. 3) while the breast 44 is being irradiated with the radiation X.

The radiation X that has passed through the presser plate 38, the breast 44, the moving grid 23, and the solid-state detector 24 is applied to the dose detecting sensor 52, which detects the dose of the radiation X (step S9). Data of the dose detected by the dose detecting sensor 52 is supplied to the irradiation dose calculator 64. The irradiation dose calculator 64 calculates a main-exposure-mode-required irradiation dose which is required in a main exposure mode from the pre-exposure-mode irradiation dose, which represents the dose of the radiation X detected in the pre-exposure-mode time (step S10). At this time, because the breast 44 has already been irradiated with the pre-exposure-mode irradiation dose of the radiation X in the pre-exposure mode, the irradiation dose calculator 64 calculates a main-exposure-mode-required irradiation dose from which the pre-exposure-mode irradiation dose is subtracted.

The main-exposure-mode-required irradiation dose calculated by the irradiation dose calculator 64 is supplied to the radiation source controller 56 and the grid controller 62. The radiation source controller 56 calculates a main-exposure-mode time for obtaining the main-exposure-mode-required irradiation dose (step S11). The grid controller 62 calculates a moving speed of the moving grid 23 using the calculated main-exposure-mode time and the grid speed setting table stored in the grid speed setting table memory 72 (step S12).

Thereafter, the radiation source controller 56 controls the radiation source 22 according to the calculated main-exposure-mode time to apply the radiation X to the breast 44 in the main exposure mode (step S13). At this time, the grid controller 62 controls the grid actuator 60 to move the moving grid 23 at the moving speed calculated in step S12 in the direction indicated by the arrow C (FIG. 3) while the breast 44 is being irradiated with the radiation X.

The radiation X that has passed through the presser plate 38, the breast 44, and the moving grid 23 is applied to the solid-state detector 24, which records a radiation image as electric charge information. After the radiation image of the breast 44 is captured, the reading light source 48 moves in the direction indicated by the arrow C (FIG. 3) along the solid-state detector 24 and then applies reading light, for thereby reading the radiation image recorded in the solid-state detector 24. The radiation image read from the solid-state detector 24 is supplied to the image processor 58, which processes the radiation image (step S14).

In order to prepare the solid-state detector 24 to capture a next radiation image, the solid-state detector 24 from which the radiation image has been read is irradiated with erasing light emitted from the erasing light source 50 to remove unwanted electric charges stored in the solid-state detector 24.

Figure 7:
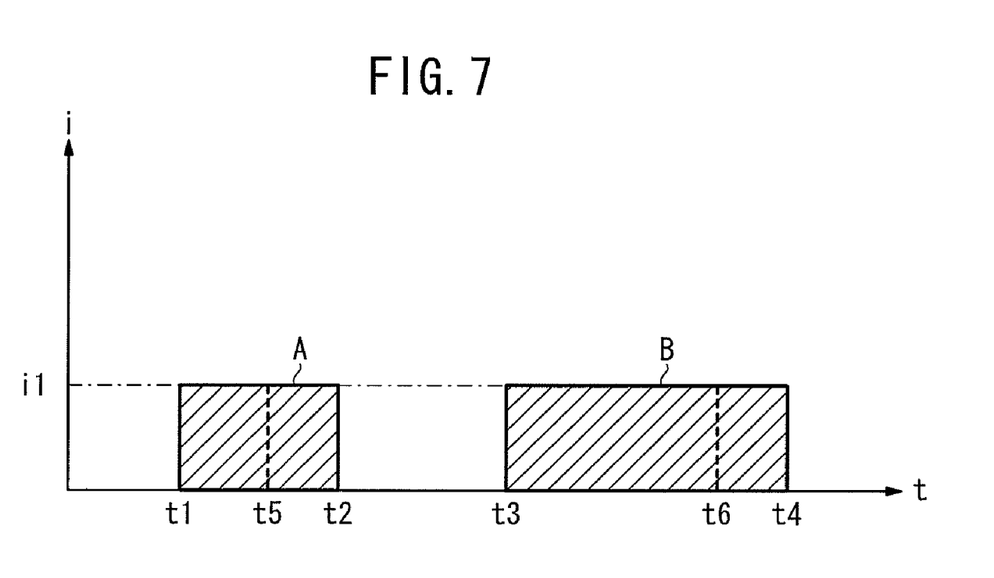
FIG. 7 is a diagram showing the relationship between the irradiation times in a pre-exposure mode and a main exposure mode for capturing a radiation image of a thin breast.
Figure 8:
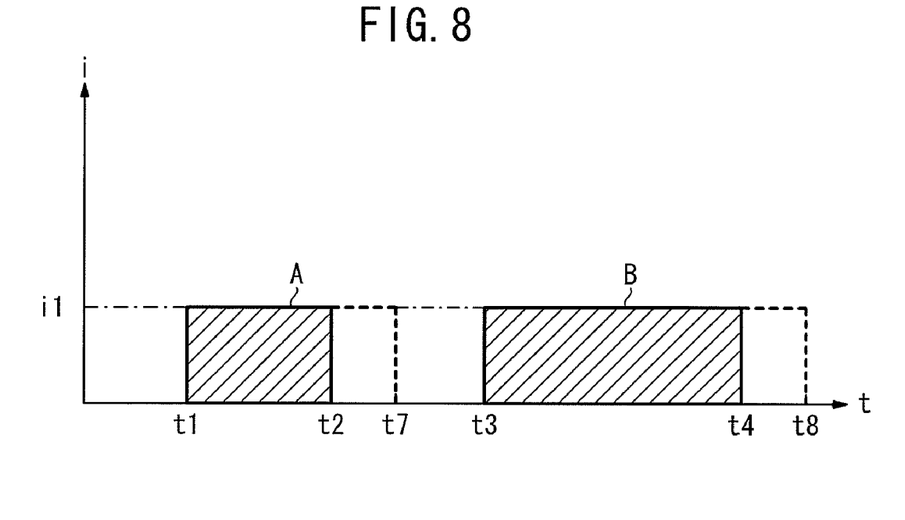
FIG. 8 is a diagram showing the relationship between the irradiation times in a pre-exposure mode and a main exposure mode for capturing a radiation image of a thick breast.

FIGS. 7 and 8 show the relationship between the irradiation time t of the radiation X and the tube current i supplied to the radiation source 22. In FIGS. 7 and 8, a pre-exposure-mode area A and a main-exposure-mode area B, both shown hatched, represent areas for producing a suitable radiation image by applying a radiation to a reference breast 44 with a tube current i1 during a pre-exposure-mode time (t2-t1) in a pre-exposure mode to establish a main-exposure-mode irradiation dose, and thereafter applying a radiation to the reference breast 44 with the tube current i1 during a main-exposure-mode time (t4-t3) in a main exposure mode.

If the thickness of the breast 44 measured by the thickness measuring unit 66 is smaller than the thickness of the reference breast 44, then in order that the dose detecting sensor 52 will not be irradiated with an excessive dose of the radiation X, a shorter pre-exposure-mode time (t5-t1) is established depending on the thickness of the breast 44 and the dose of the radiation X is detected in the shorter pre-exposure-mode time (t5-t1) for thereby calculating a main-exposure-mode-required irradiation dose highly accurately (see FIG. 7). Since the thickness of the breast 44 is smaller, a required main-exposure-mode time (t6-t3) is also shorter. The moving speed of the moving grid 23 is adjusted according to the pre-exposure-mode time and the main-exposure-mode time.

If the thickness of the breast 44 measured by the thickness measuring unit 66 is greater than the thickness of the reference breast 44, then in order that the dose detecting sensor 52 will be irradiated with a detectable dose of the radiation X, a longer pre-exposure-mode time (t7-t1) is established depending on the thickness of the breast 44 and the dose of the radiation X is detected in the longer pre-exposure-mode time (t7-t1) for thereby calculating a main-exposure-mode-required irradiation dose highly accurately (see FIG. 8). Since the thickness of the breast 44 is greater, a required main-exposure-mode time (t8-t3) is also longer.

Figure 9:
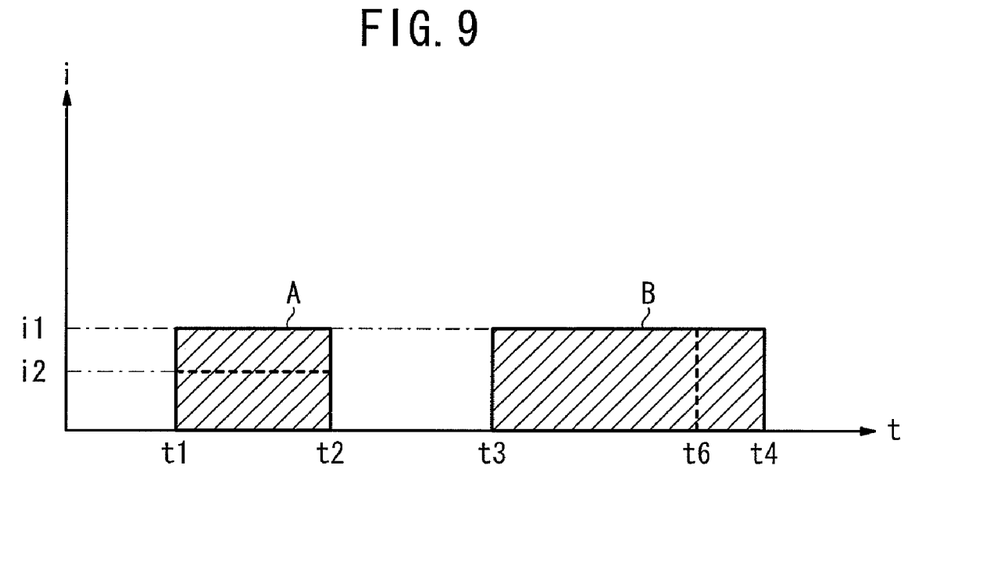
FIG. 9 is a diagram showing controlled tube currents in a pre-exposure mode and a main exposure mode for capturing a radiation image of a thin breast.
Figure 10:
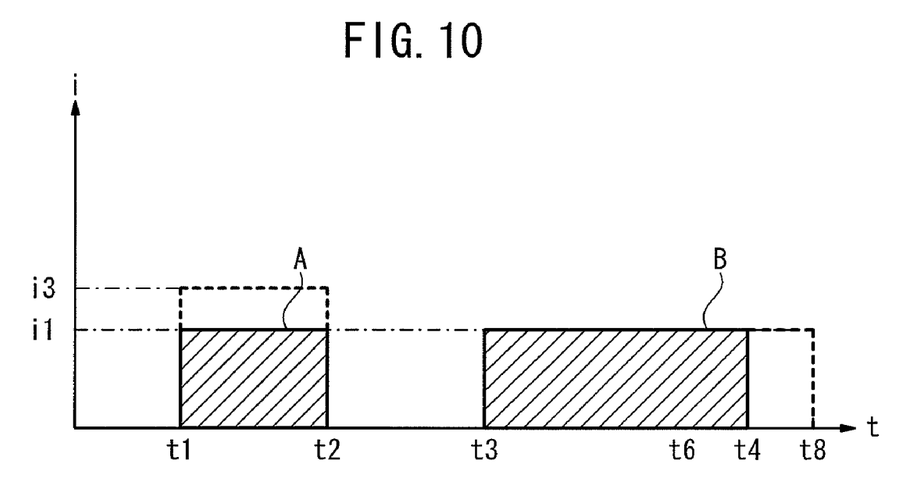
FIG. 10 is a diagram showing controlled tube currents in a pre-exposure mode and a main exposure mode for capturing a radiation image of a thick breast.
Figure 11:
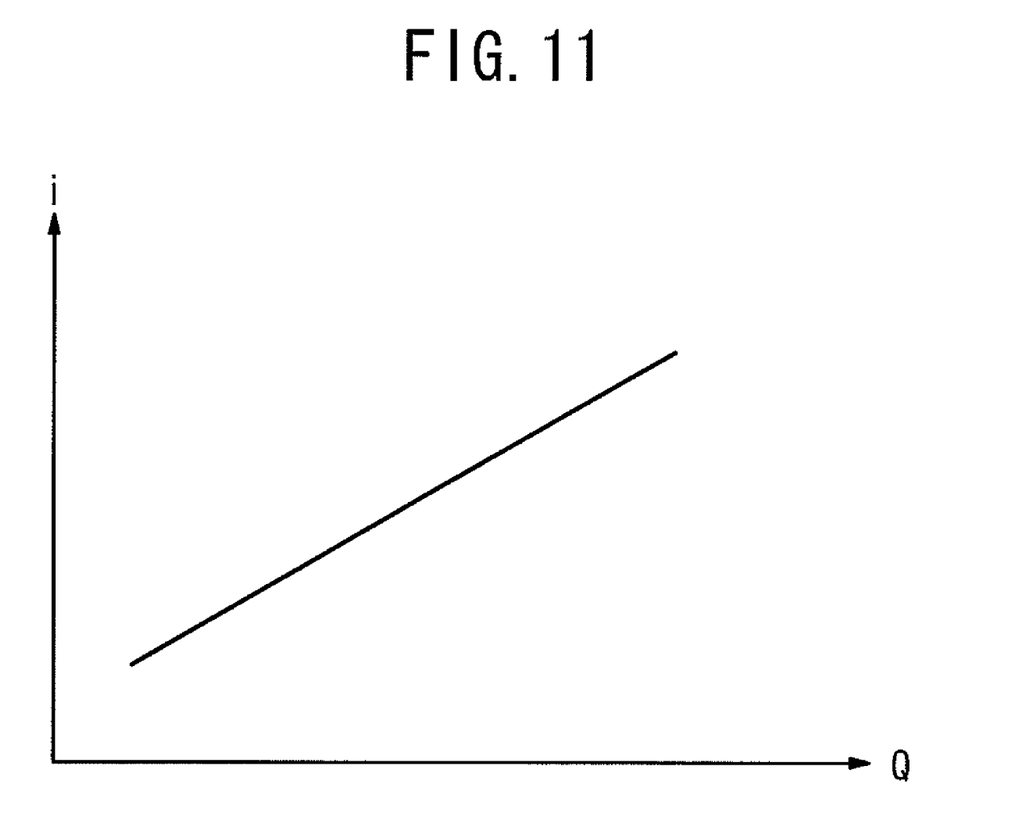
FIG. 11 is a graph showing the relationship between the required irradiation dose and the tube current.

FIGS. 9 and 10 are illustrative of a process of controlling the tube current i rather than the pre-exposure-mode time in the pre-exposure mode for the radiation X. FIG. 11 shows the relationship between the irradiation dose Q of the radiation X which is required to be detected by the dose detecting sensor 52 or the solid-state detector 24 and the tube current i for obtaining the irradiation dose Q.

For example, if the thickness of the breast 44 is smaller than the thickness of the reference breast 44, then in order to obtain a pre-exposure-mode-required irradiation dose, the tube current i1 is changed to a tube current i2 (i1>i2) depending on the thickness of the breast 44, and the breast 44 is irradiated with the radiation X based on the tube current i2 in the pre-exposure mode for thereby calculating a main-exposure-mode-required irradiation dose highly accurately (see FIG. 9). Similarly, in the main exposure mode, the tube current can also be adjusted depending on the main-exposure-mode-required irradiation dose.

If the thickness of the breast 44 is greater than the thickness of the reference breast 44, then the tube current i1 is changed to a tube current i3 (i3>i1) depending on the thickness of the breast 44, and the breast 44 is irradiated with the radiation X based on the tube current i3 in the pre-exposure mode for thereby calculating a main-exposure-mode-required irradiation dose highly accurately (see FIG. 10). Similarly, in the main exposure mode, the tube current can also be adjusted depending on the main-exposure-mode-required irradiation dose.

If the tube current is controlled while the pre-exposure-mode time (t2-t1) is being fixed, then irregularities are prevented from being introduced into the radiation image by the moving grid 23 without the need for controlling the moving speed of the moving grid 23.

The mammographic system 20 may employ, instead of the light-reading solid-state detector 24, a radiation detector for directly reading electric charge information representing a stored radiation image as an electric signal or a stimulable phosphor panel.

Although certain preferred embodiments of the present invention have been shown and described in detail, it should be understood that various changes and modifications may be made therein without departing from the scope of the appended claims.

What is claimed is:

1. An apparatus for capturing a radiation image by applying a radiation emitted from a radiation source to a breast and detecting the radiation that has passed through the breast with a radiation detector, comprising:
   a dose detecting sensor for detecting a dose of said radiation that has passed through the breast;
   a thickness measuring unit for measuring a thickness of the breast along a direction in which the radiation passes through the breast, when the breast is pressed against said radiation detector by a presser plate;
   a pre-exposure-mode-required irradiation dose calculator for calculating a pre-exposure-mode-required irradiation dose required to apply said radiation to the breast in a pre-exposure mode prior to a main exposure mode for capturing said radiation image, using the measured thickness of the breast as a parameter;
   a main-exposure-mode-required irradiation dose calculator for calculating a main-exposure-mode-required irradiation dose required to apply said radiation to the breast in the main exposure mode, based on a pre-exposure-mode irradiation dose which represents the dose of said radiation detected by said dose detecting sensor in said pre-exposure mode; and
   a radiation source controller for controlling said radiation source to apply said radiation to the breast in said pre-exposure mode according to the calculated pre-exposure-mode-required irradiation dose and controlling said radiation source to apply said radiation to the breast in said main exposure mode according to the calculated main-exposure-mode-required irradiation dose.

2. An apparatus according to claim 1, further comprising:
   a radiation quality information setting unit for setting radiation quality information of said radiation applied to the breast;
   wherein said pre-exposure-mode-required irradiation dose calculator calculates the pre-exposure-mode-required irradiation dose using said radiation quality information as a parameter.

3. An apparatus according to claim 1, further comprising:
   a pressure measuring unit for measuring a pressure applied to the breast by said presser plate;
   wherein said pre-exposure-mode-required irradiation dose calculator calculates the pre-exposure-mode-required irradiation dose using said pressure as a parameter.

4. An apparatus according to claim 1, further comprising:
   a moving grid for removing scattered rays of said radiation applied to said radiation detector; and
   a grid controller for controlling a moving speed of said moving grid in said pre-exposure mode according to the calculated pre-exposure-mode-required irradiation dose.

5. An apparatus according to claim 4, wherein said grid controller controls the moving speed of said moving grid in said main exposure mode according to the calculated main-exposure-mode-required irradiation dose.

6. An apparatus according to claim 1, wherein said radiation source controller controls a tube current supplied to said radiation source in said pre-exposure mode according to the calculated pre-exposure-mode-required irradiation dose.

7. An apparatus according to claim 6, wherein said radiation source controller controls a tube current supplied to said radiation source in said main exposure mode according to the calculated main-exposure-mode-required irradiation dose.

8. An apparatus according to claim 1, wherein said dose detecting sensor comprises said radiation detector.

9. A method of capturing a radiation image by applying a radiation emitted from a radiation source to a breast and detecting the radiation that has passed through the breast with a radiation detector, comprising the steps of:
   measuring a thickness of the breast along a direction in which the radiation passes through the breast, when the breast is pressed against said radiation detector by a presser plate;
   calculating a pre-exposure-mode-required irradiation dose required to apply said radiation to the breast in a pre-exposure mode prior to a main exposure mode for capturing said radiation image, using the measured thickness of the breast as a parameter;
   controlling said radiation source to apply said radiation to the breast in the pre-exposure mode according to the calculated pre-exposure-mode-required irradiation dose, and detecting a pre-exposure-mode irradiation dose of the radiation which has passed through the breast;
   calculating a main-exposure-mode-required irradiation dose required to apply said radiation to the breast in the main exposure mode, based on the pre-exposure-mode irradiation dose detected in said pre-exposure mode; and
   controlling said radiation source to apply said radiation to the breast in said main exposure mode according to the calculated main-exposure-mode-required irradiation dose.

10. A method according to claim 9, wherein said pre-exposure-mode-required irradiation dose is calculated using radiation quality information of said radiation applied to the breast, as a parameter.

11. A method according to claim 9, wherein said pre-exposure-mode-required irradiation dose is calculated using a pressure applied to the breast by said presser plate, as a parameter.

12. A method according to claim 9, further comprising the step of controlling a moving speed, in said pre-exposure mode, of a moving grid for removing scattered rays of said radiation applied to said radiation detector, according to the calculated pre-exposure-mode-required irradiation dose.

13. A method according to claim 12, further comprising the step of controlling the moving speed, in said main-exposure mode, of said moving grid according to the calculated main-exposure-mode-required irradiation dose.

14. A method according to claim 9, further comprising the step of controlling a tube current supplied to said radiation source in said pre-exposure mode according to the calculated pre-exposure-mode-required irradiation dose.

15. A method according to claim 14, further comprising the step of controlling the tube current supplied to said radiation source in said main exposure mode according to the calculated main-exposure-mode-required irradiation dose.

* * * * *